United States Patent
Thommes et al.

(10) Patent No.: US 7,220,356 B2
(45) Date of Patent: May 22, 2007

(54) METHOD OF PURIFYING POLYPEPTIDES BY SIMULATED MOVING BED CHROMATOGRAPHY

(75) Inventors: Jörg Thommes, San Diego, CA (US); John P. Pieracci, San Diego, CA (US); Marc Bisschops, Breda (NL); Alan M. Sonnenfeld, San Diego, CA (US); Lynn Conley, Escondido, CA (US); Marten Pennings, The Hague (NL)

(73) Assignee: Biogen Idec Inc., Cambridge, MA (US)

( * ) Notice: Subject to any disclaimer, the term of this patent is extended or adjusted under 35 U.S.C. 154(b) by 0 days.

(21) Appl. No.: 10/661,086

(22) Filed: Sep. 12, 2003

(65) Prior Publication Data

US 2004/0241878 A1 Dec. 2, 2004

Related U.S. Application Data

(60) Provisional application No. 60/410,506, filed on Sep. 13, 2002.

(51) Int. Cl.
*B01D 15/08* (2006.01)
(52) U.S. Cl. .................. 210/635; 210/659; 210/198.2; 530/413
(58) Field of Classification Search ................ 210/635, 210/656, 659, 198.2; 530/413
See application file for complete search history.

(56) References Cited

U.S. PATENT DOCUMENTS

| | | | | |
|---|---|---|---|---|
| 4,016,149 A | * | 4/1977 | Travis et al. ................. 530/364 |
| 4,430,496 A | * | 2/1984 | Abbott ..................... 536/26.73 |
| 5,240,602 A | * | 8/1993 | Hammen .................. 210/198.2 |
| 5,645,729 A | * | 7/1997 | Priegnitz et al. ............ 210/659 |
| 5,770,088 A | | 6/1998 | Ikeda et al. ................. 210/659 |
| 5,959,085 A | * | 9/1999 | Garrone et al. ........... 530/387.3 |
| 6,149,874 A | * | 11/2000 | Hotier ......................... 422/142 |
| 6,306,306 B1 | * | 10/2001 | Voigt et al. ................. 210/635 |
| 6,479,300 B1 | * | 11/2002 | Jiang et al. ................. 436/518 |
| 6,572,767 B2 | * | 6/2003 | Stipanovic et al. ....... 210/198.2 |
| 6,641,735 B1 | * | 11/2003 | Yoshizako et al. .......... 210/635 |
| 6,727,275 B2 | * | 4/2004 | Zou et al. .................... 514/423 |
| 6,805,799 B2 | * | 10/2004 | Ma ............................ 210/659 |
| 6,936,633 B2 | * | 8/2005 | Zou et al. .................... 514/424 |
| 2003/0036637 A1 | * | 2/2003 | Fulton ........................ 530/363 |

(Continued)

FOREIGN PATENT DOCUMENTS

WO WO 01/37959 A1 5/2001

OTHER PUBLICATIONS

Gottschlich et al., "Purification of monoclonal antibodies by simulated moving-bed chromatography," J. Chromatogr. A, 1997, 765(2):201-6.

(Continued)

*Primary Examiner*—Ernest G. Therkorn
(74) *Attorney, Agent, or Firm*—Pillsbury Winthrop Shaw Pittman LLP

(57) ABSTRACT

Provided are methods of separating an immunoreactive compound from at least one immaterial component, using a simulated moving bed ("SMB") system and a SMB apparatus for use in these methods. Also provided are purified immunoreactive compounds prepared using the SMB methods and apparatus and methods of treatment with the purified immunoreactive compounds.

11 Claims, 12 Drawing Sheets

U.S. PATENT DOCUMENTS

2003/0149081 A1    8/2003    Zou et al. .................. 514/343

OTHER PUBLICATIONS

Fulton et al.; "The Challenge of Recombinant hSA (Ton-scale production of recombinant protein pharmaceuticals)," presented at *Recovery of Biological Products X*, Cancun, Mexico (Jun. 2001).

D.K. Roper et al., "Separation of biomolecules using adsorptive membranes" (1995) J. Chromatography A, 702:3-26.

Supplementary European Search Report, issued Jun. 19, 2006, for European Patent Application No. 03754547.2, based on International Patent Application No. PCT/US03/28809.

G. Rossiter, "Continuous processing using solid adsorbents, ," Trends in Downstrean Processing for Biotechnology, Technologische Instituut in collaboration with the Dutch Biotechnology Association (NBV) (Lakeland Florida), p. 1-18, (1997).

Marc Bisschops, PHD, "Industrial Scale Applications of Continuous Chromatography," presented at the Advanced Course in Downstream Processing, p. 1-13 , (2001).

\* cited by examiner

METHOD OF PURIFYING POLYPEPTIDES BY SIMULATED MOVING BED CHROMATOGRAPHY

CROSS REFERENCE TO RELATED APPLICATIONS

Priority is claimed under 35 U.S.C. §119(e) of U.S. Provisional Patent Application No. 60/410,506, filed Sep. 13, 2002.

FIELD OF THE INVENTION

The present invention is directed to methods of purifying polypeptides using simulated moving bed chromatography and to simulated moving bed chromatography systems and apparatus suitable for purifying polypeptides.

BACKGROUND AND INTRODUCTION TO THE INVENTION

Chromatographic separations used for protein purification are traditionally performed in batch mode, i.e. a single packed column is used and equilibration, load, wash, elution and regeneration/cleaning are performed sequentially. This mode leads to a comparatively long process with fairly low overall throughput. In addition, due to kinetic limitations of protein adsorption, in a batch mode, chromatography columns are loaded only to their so-called dynamic capacity which usually is 30 to 50% of their equilibrium capacity. This in turn requires using columns of two to three times the volume than would be needed if the columns were operated in equilibrium. Since protein chromatography resins are very expensive, this has major economic consequences adding to the cost of purification of product. Additionally, wash and elution processes in batch column chromatography require substantial fluid volumes, which is also due to the batch mode of operation which has economic consequences since the purified water used must be specially treated.

Simulated Moving Bed (SMB) chromatography has been used in the petrochemical and mineral industries. SMB chromatography has also found application in the pharmaceutical industry for the separation of enantiomers.

Other applications of SMB chromatography include, for example, the separation of fructose from fructose-glucose solutions and the separation of sucrose from sugar beet or sugar cane syrups. Solution components are differentially absorbed by the ion exchange resin so that a separation waveform develops within the simulated moving bed.

SUMMARY OF THE INVENTION

The present invention is directed to methods of purifying immunoreactive proteins by separation from at least one immaterial component using simulated moving bed ("SMB") chromatography, to SMB systems and to apparatus useful in these methods, to immunoreactive proteins separated by SMB chromatography and to methods of treating patients with the separated immunoreactive proteins.

In one aspect, the present invention is directed to a method of separating an immunoreactive compound from at least one immaterial component in a fluid mixture using simulated moving bed chromatography. According to this aspect, the method comprises the steps of: (a) providing a simulated moving bed apparatus that comprises a plurality of modules in fluid conducting communication, said modules comprising at least one solid phase; (b) continuously introducing the fluid mixture into said simulated moving bed apparatus wherein the fluid mixture contacts the solid phase in a countercurrent mode; (c) effecting separation of the immunoreactive compound from at least one immaterial component; and (d) collecting the immunoreactive compound to provide a purified composition thereof. According to one embodiment of this aspect, the immunoreactive compound associates with the solid phase to a greater or lesser degree than at least one immaterial component. Preferably, the immunoreactive compound associates with the solid phase to a greater degree than at least one immaterial component. According to an alternate embodiment, this method further comprises the step of effecting said separation by contacting the solid phase with an eluent that promotes disassociation of the immunoreactive compound. Suitable eluents include an acidic buffer. Suitable solid phases include a support material associated with Protein A or Protein G. The separation may be effected using chromatographic methods such as adsorption chromatography, partition chromatography, ion exchange chromatography, size exclusion chromatography or affinity chromatography. Preferably, separation is effected using affinity chromatography. The present invention is also directed to an immunoreactive compound prepared according to these methods.

In another aspect, the present invention is directed to a simulated moving bed ("SMB") system for separating an immunoreactive compound from at least one immaterial component when both are present in a fluid mixture. According to this aspect the SMB system incorporates a plurality of zones comprising a solid phase which is contacted countercurrently by said fluid mixture and wherein said zones comprise (i) an association zone wherein the immunoreactive compound and at least one immaterial component differentially associate with the solid phase; (ii) a wash zone wherein at least one immaterial component is preferentially disassociated from the solid phase; and (iii) an elution zone wherein the immunoreactive compound is preferentially disassociated from the solid phase. According to one embodiment, the wash zone is intermediate between the association zone and the elution zone. The solid phase may preferentially associate with the immunoreactive compound. According to one aspect of this embodiment, the solid phase comprises a ligand for affinity chromatography. Suitable solid phases may comprise Protein A or Protein G. An alternate suitable solid phase comprises a cation exchange resin. According to one aspect of this embodiment, the simulated moving bed system further comprises an elution wash zone intermediate between the elution zone and the association zone. Also, this embodiment may further comprise a regeneration zone and intermediate between the elution wash zone and the association zone and also an equilibration zone intermediate between the regeneration zone and the association zone. The present invention is also directed to a method of separating an immunoreactive compound from at least one immaterial component which comprises using simulated moving bed systems and to a purified immunoreactive compound prepared using such simulated moving bed systems.

According to a further aspect, the present invention is directed to a method of separating an antibody from at least one immaterial component in a fluid mixture where both are present using simulated moving bed chromatography which comprises the steps of (a) providing a simulated moving bed apparatus that comprises a plurality of modules in fluid conducting communication, said modules comprising at least one solid phase which comprises an affinity chromatography ligand which preferentially associates with the antibody; (b) continuously introducing the fluid mixture into the simulated moving bed apparatus wherein the fluid mixture contacts the solid phase in a countercurrent mode; (c) effecting separation of the antibody from at least one immaterial component; and (d) collecting the antibody to provide a purified composition thereof.

In an additional aspect, the present invention is directed to a simulated moving bed ("SMB") system for separating an antibody from at least one immaterial component where both are present in a fluid mixture. According to this aspect, the SMB system incorporates a plurality of zones comprising a solid phase comprising an affinity resin which is contacted countercurrently by the fluid mixture and wherein said zones comprise: (i) an association zone wherein the antibody and at least one immaterial component differentially associate with the solid phase; (ii) a first wash zone wherein at least one immaterial component is preferentially dissociated from the solid phase; and (iii) an elution zone wherein the antibody is preferentially disassociated from the solid phase.

In another aspect, the present invention is directed to a method of separating an immunoreactive compound from at least one immaterial component in a fluid mixture using simulated moving bed chromatography comprising the steps of: (a) providing a simulated moving bed apparatus which comprises at least one module in fluid conducting communication with said apparatus, said module comprising at least one solid phase and wherein said apparatus comprises a plurality of zones through which the modules pass; (b) continuously introducing the fluid mixture into the module in an association zone wherein the fluid mixture contacts the solid phase in a countercurrent mode and wherein the immunoreactive compound associates with the solid phase; (c) continuously introducing a wash buffer into the module comprising the associated immunoreactive compound in a wash zone wherein the wash buffer contacts the solid phase in a countercurrent mode and substantially removes at least one immaterial component from said module; (d) continuously introducing an elution buffer into the module comprising the associated immunoreactive compound in an elution zone wherein the elution buffer contacts the solid phase in a countercurrent mode and whereby the immunoreactive compound is substantially disassociated from the solid phase; and (e) continuously removing a product stream comprising the immunoreactive compound from the module. According to one embodiment, the simulated moving bed apparatus comprises a plurality of modules. Preferably, solid phase comprises an affinity ligand. Suitable affinity ligands include Protein A or Protein G. According to one aspect, the immunoreactive compound comprises an antibody or antibody fragment. The present invention is also directed to a purified antibody or antibody fragment prepared substantially by these methods.

According to another aspect, the present invention provides an improved method of purifying an immunoreactive compound from at least one immaterial component, the improvement which comprises using simulated moving bed affinity chromatography with a solid phase comprising Protein A or Protein G.

Suitable immunoreactive compounds to be separated using the SMB methods of the present invention include antibodies and antibody fragments. Such immunoreactive compounds include those which bind to an antigen selected from the group consisting of CD20, CD40, CD40L, CD23, CD4, CD80 and CD86.

Definitions

In accordance with the present invention and as used herein, the following terms are defined to have the following meanings, unless explicitly stated otherwise:

The term "immunoreactive compound" refers to a compound which comprises an antigen binding region and/or a constant region from an immunoglobulin. In one aspect, included is a compound which binds to an antigen. An immunoreactive compound may additionally comprise peptide sequences from non-antibody compounds, such as cytokines, cytokine ligands and other antigens. Such immunoreactive compounds include antibodies, antibody fragments, domain-deleted antibodies, or an antibody linked to another specific binding member or mixtures thereof. Domain-deleted antibodies include compounds such as those described in WO 02/060995, the disclosure of which is incorporated herein by reference. Other immunoreactive compounds include fusion proteins which comprise a region of an immunoglobulin chain fused to an amino acid sequence such as an amino acid sequence of a ligand binding partner or an amino acid sequence variant of an adhesion. Such fusion proteins include those described in U.S. Pat. Nos. 5,428,130 and 5,565,335, the disclosures of which are incorporated by reference herein.

The term "antibody" herein is used in the broadest sense and specifically covers intact monoclonal antibodies, polyclonal antibodies, multispecific antibodies (e.g. bispecific antibodies) formed from at least two intact antibodies, humanized antibodies, primatized antibodies, domain-deleted antibodies, and antibody fragments so long as they exhibit the desired biological activity.

"Antibody fragments" comprise a portion of an intact antibody, preferably comprising the antigen binding or variable region thereof. Examples of antibody fragments include Fab, Fab', F(ab')Z, and Fv fragments; diabodies; linear antibodies; single chain antibody molecules; and multispecific antibodies formed from antibody fragments. Domain deleted antibodies comprising immunoglobulins in which at least part of one or more constant regions have been altered or deleted to provide modified physiological properties (e.g. reduced serum half-life) may also be considered antibody fragments for the purposes of the instant disclosure. In preferred embodiments the domain deleted antibodies will comprise constant regions that lack the $C_H2$ domain.

"Chromatography" refers to any analytical technique used for the chemical separation of mixtures and components, that relies upon selective attraction among the components of a mixture for a solid phase. Examples include adsorption chromatography, partition chromatography, ion exchange chromatography, size exclusion chromatography, and affinity chromatography.

"Adsorbent" is used herein generically to refer to the solid phase used in chromatography for which the mobile phase components exhibit a selective affinity. Because such affinity can take a variety of forms other than adsorption (including size exclusion or complexation), the term refers to solid phases that adsorb the components of a mixture and to solid phases that do not technically adsorb components from the mobile phase, but which nevertheless behave as an adsorbent by slowing the migration velocity of one component relative to another in a chromatographic system.

"Purified" when referring to a component or fraction indicates that its relative concentration (weight of component or fraction divided by the weight of all components or fractions in the mixture) is increased by at least 20%. In one series of embodiments, the relative concentration is increased by at least 40%, 50%, 60%, 75%, 100%, 150%, or 200%. A component or fraction can also be said to be purified when the relative concentration of components from which it is purified (weight of component or fraction from which it is purified divided by the weight of all components or fractions in the mixture) is decreased by at least 20%, 40%, 50%, 60%, 75%, 85%, 95%, 98% or 100%. In still another series of embodiments, the component or fraction is purified to a relative concentration of at least 50%, 65%, 75%, 85%, 90%, 97%, 98%, or 99%. When a component or fraction in one embodiment is "separated" from other components or fractions, it will be understood that in other embodiments the component or fraction is "purified" at levels provided herein.

"Module" refers to a portion of a simulated moving bed apparatus. A module may comprise one or a plurality of columns or vessels.

"Ring" is used to describe how the modules of a SMB system are configured in relation to one another in the SMB system because the output of each module comprises the input for the successive module, in a circular fashion. The term "ring" should thus not be understood to be limited to a circular configuration of the modules and columns within the modules.

"Multicomponent mixture" refers to a fluid mixture that comprises three or more components or fractions which can be separated using a prescribed chromatographic process, because each component or fraction displays a different affinity for the adsorbent employed.

"Immaterial component" refers to a component present in the fluid mixture containing the immunoreactive compound which is not an immunoreactive compound and which is separated from immunoreactive component. Immaterial components may include host cell protein (HCP), antibiotics and other components present in the fluid mixture.

"Mass transfer effects" refer generally to those physical phenomena which cause components of a mixture to display distinct dispersion behavior from the mixture in a given system, and to depart from the ideal system. Mass transfer effects thus include those effects modeled using axial dispersion coefficients, intraparticle diffusion coefficients, and film mass transfer coefficients. Mass transfer effects thus also include fronting and dispersion due to extra-column dead volume. A separation is hindered by non-negligible mass transfer effects if the mass transfer correction term, discussed in more detail below, is more than 2% of the mobile phase velocity in any of the zones as prescribed by equations 3–6 (the mobility phase velocities for an ideal system), to achieve a prescribed purity and yield. The designs of the present invention can also extend to systems in which the mass transfer correction velocity increases or decreases the mobile phase velocity for the ideal system by more than 1, 3, 5, 7.5, 10, 15, 20, 30, 50, 75, 100%, 200%, 400%, 600%, 1000%, or more.

As used herein, "substantially separated from other components" means that the separated component contains no more than about 20% by weight of each other component, preferably no more than about 5% by weight of each other component, and more preferably no more than about 1% by weight of each other component.

As used herein, "a stream that does not contain substantial amounts of a component" means that the stream contains at most about 20% by weight of the component, preferably at most about 5% by weight of the component, and more preferably at most about 1% by weight of the component.

BRIEF DESCRIPTION OF THE DRAWINGS

FIG. 8 represents a two dimensional depiction of a carousel apparatus wherein the columns are arranged in a circle.

DETAILED DESCRIPTION OF THE INVENTION

Figure 1:
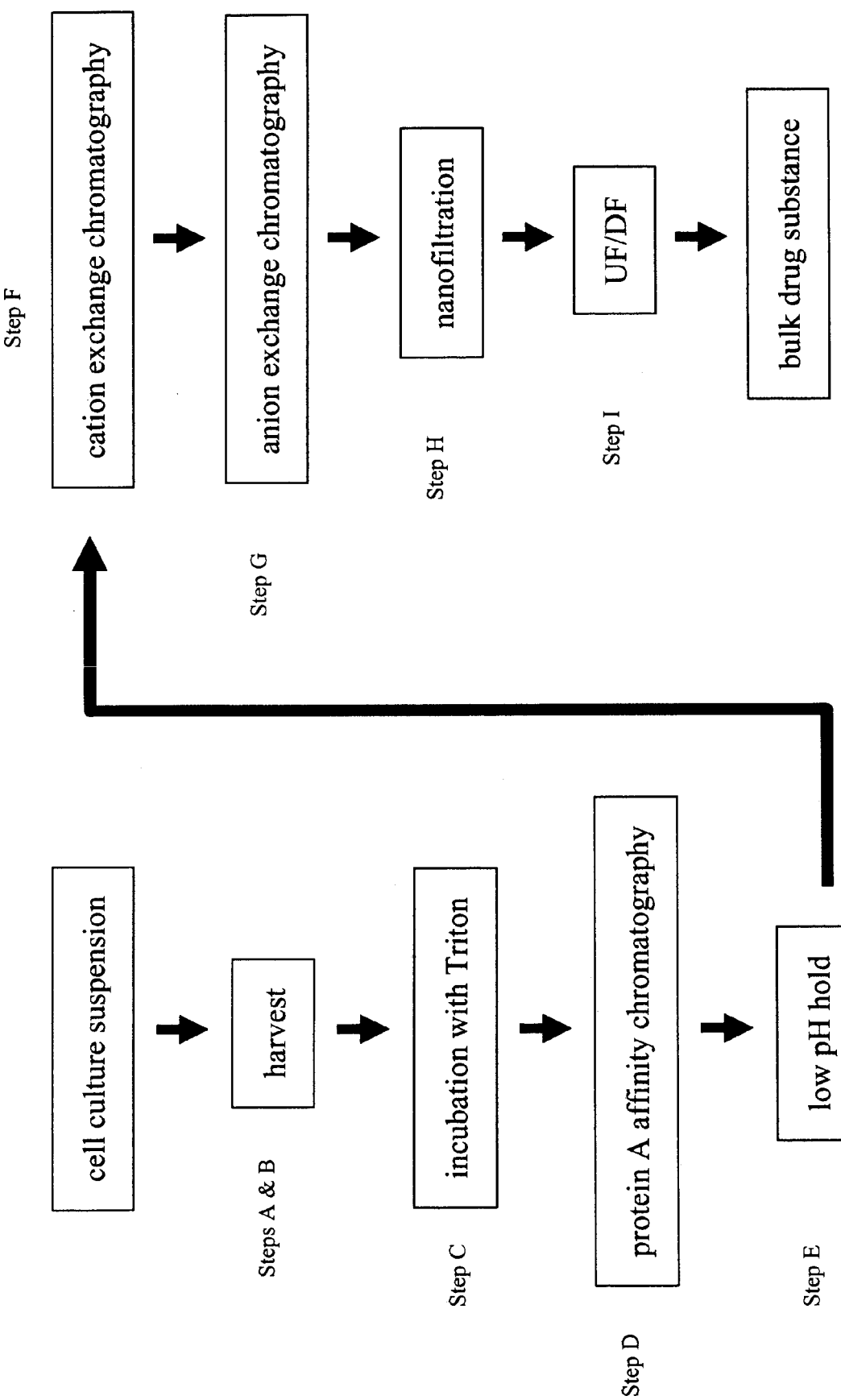
FIG. 1 depicts a flow chart of a general procedure for isolation and purification of an immunoreactive compound, such as an antibody produced in cell culture.

According to one aspect, the present invention is directed to simulated moving bed ("SMB") systems and to simulated moving bed chromatography methods suitable for use in a process of isolating and separating immunoreactive compounds, such as antibodies made in cell culture. The SMB systems and methods of the present invention may be used in a process such as that depicted in FIG. 1 for either Step D or Step F or FIG. 2 for either Step B or D.

These processes typically incorporate one or more chromatography steps. Since protein chromatography resins are very expensive, the use of chromatography columns in a batch mode loaded only to their so-called dynamic capacity (which usually is 30 to 50% of their equilibrium capacity), requires using columns of two to three times the volume than would be needed if the columns were operated in equilibrium (i.e., loaded to their equilibrium capacity). Thus, use of a batch mode for the chromatography steps has major economic consequences. Additionally, wash and elution processes in batch column chromatography require substantial fluid volumes, which is also due to the batch mode of operation. Use of continuous chromatography, in a continuous, counter-current mode where the columns are loaded to equilibrium capacity would require smaller column volumes. Additionally more efficient wash and elution processes would lead to substantially reduced consumption of buffers. One way of putting this into practice is use simulated moving bed chromatography.

A typical simulated moving bed system has at least one module or a plurality of modules filed with solid phase. A module may include one or a plurality of columns or vessels. Fluid conduits interconnect the upstream and downstream ends of the system to form a loop through which a fluid mixture is continuously circulated. At certain points liquid streams may be introduced and at other points effluent streams may be withdrawn. The constant flow of fluid through the loop is called "internal recirculation flow." A manifold system of pipes and valves is provided selectively to position an inlet for feed material, an inlet for elution buffer (to disassociate a component from the solid phase), an outlet for a disassociated component and an outlet for an unassociated (or less associated) component. Each inlet and outlet communicates with a separate module (or vessel or column). Feed material enters the system at a designated point and is moved through the solid phase by the continuous internal recirculation flow. This moving contact results in a chromatographic separation of components. Unassociated component(s) which flow(s) at a relatively fast rate are removed from an unassociated component outlet, such as by removal of a first wash effluent stream. A buffer which disassociates an associated compound from the solid phase (elution buffer) is added at its inlet value between the respective outlet valve positions of the associated and unassociated components.

At predetermined time intervals (switch time) the designated inlet and outlet valve positions are displaced downstream one position on the manifold to the next solid phase bed module, which may be a discrete section of a vessel, (such as a column), or an individual vessel, e.g., column. The step time is chosen such that the designation of valves is properly synchronized with the internal recirculation flow. Under these conditions the system eventually reaches a steady state with specific product characteristics appearing at predetermined intervals in sequence at each valve position. This type of system simulates valves held in a single position while the solid phase moves at a constant and continuous rate around the recirculation loop producing constant quality product at each valve. An alternative apparatus actually intermittently moves the columns—often mounted on a carousel—while the valve locations are fixed.

The simulated version more closely approaches the character of an actual moving bed system as the number of modules (or vessels or columns) and valve positions increase. An important distinction between batch and simulated moving bed system is that the internal recirculation flow is continuous in the simulated moving bed process. Except for very small adjustments to control internal pressure, the entering and exiting flow rates are continuous and constant, thereby approximating an actual moving bed system as closely as possible.

An equilibrated SMB system exhibits a steady state component separation waveform along the path of the recirculation loop. This waveform moves along the path of the recirculation loop with valve switching synchronized to maintain the desired steady state. In such a SMB system the zones may be viewed as stationary with the modules moving through the zones.

Simulated moving bed processes realize the countercurrent movement of solid and liquid phases and the concomitant advantages of continuous moving beds over batch chromatography without the physical movement of solids. SMB processes utilize a series of modules comprising at least one solid phase connected to form a circuit. In some systems, each module contains at least one or two or more evenly sized columns, and these columns are connected to form a continuous circuit. The solid phase movement is simulated by periodically moving the inlet and outlet ports one module (of if the module comprises a plurality of columns, one column) forward in the direction of flow of the mobile (fluid) phase, so that the product ports are always near the partially separated concentration waves of products in the system. Similar to the continuous moving bed system, the port switching time, zone length, and zone flow rates are all balanced to attain a desired level of purity of the product stream. Thus, the zones may be viewed as stationary with the modules moving through one zone to another.

1. General Immunoreactive Protein Separation Processes

The SMB methods of the present invention are useful as part of a method for the separation of immunoreactive compounds, such as antibodies made by cell cultures, from immaterial component(s).

FIG. 1 depicts a schematic for a general process for the separation and isolation of immunoreactive compounds such as antibodies produced by cell culture from at least one immaterial component. The methods of the present invention may be used as a separation step in this general method or as a separation step in other general processes used in the art to isolate and purify immunoreactive compounds such as antibodies produced by recombinant and cell culture methods.

According to the process depicted in FIG. 1, the cell culture suspension in Step A is treated to harvest cells. In Step B, the cell culture suspension is clarified (cells, cell debris and precipitates are removed). One suitable method for step B is depth filtration; other suitable methods include centrifugation and tangential flow filtration. In Step C the filtrate is incubated with Triton X-100, suitably in a vessel such as in a holding tank. Treatment with Triton X-100 is believed to inactivate viruses which may be present. In Step D, the filtrate containing at least one immaterial component, such as host cell protein ("HCP"), and immunoreactive compound undergoes simulated moving bed chromatography according to the methods of the present invention in order to remove host cell protein ("HCP") and other immaterial components. Preferably affinity chromatography is employed. According to a preferred aspect, a solid phase which comprises Protein A or Protein G is employed. Any Protein A or Protein G affinity adsorbent may be used having either native or recombinant Protein A or Protein G with any conventionally used solid phase backbone (including, e.g., agarose, controlled pure glass, synthetic organic polymer, etc.). According to one aspect the solid phase comprises a recombinant Protein A. Suitable solid phases include those Prosept rA (Millipore, Bedford, Mass.) and MabSelect (Amersham Biosciences, Uppsala, Sweden). Other solid phases known to those of skill in the art for separating an immunoreactive compound, such as an antibody, from HCP and other immaterial components may be used. In Step E, the product stream is subjected to a low pH incubation step. A holding tank may be conveniently used for this step. Incubation at low pH according to this step is believed to inactivate viruses which may be present in the solution. Step F comprises cation exchange chromatography, preferably with a cation exchange solid phase using a bind and elute mode. Suitable cation exchange solid phases include strong cation exchange adsorbents including SP Sepharose XL resins using composite materials such as Hyper D (Biosepra), and tentacle resins (Merck or Tosohaas), and weak cation exchange adsorbents using carboxymethyl (CM) ligands. The SMB methods of the present invention may be used in this separation step (as well as Step D). Step F is believed to remove leached Protein A (where Step D uses affinity chromatography with a solid phase comprising Protein A) and also to remove viruses if present and other contaminants. Step G comprises anion exchange chromatography, preferably using a strong anion exchange solid phase in a flow through mode. Suitable solid phases include Fractogel TMAC. Step G is believed to remove residual contaminants (including DNA) and viruses if present due to adsorption to the anion exchanger. Step H comprises a nanofiltration step. Suitable methods include dead end filtration. Step H is believed to remove viruses which may be present by size exclusion. Step I comprises an ultrafiltration or diafiltration step. Step I is used to adjust concentration of antibody in solution to an appropriate concentration for storage and, if indicated, effect buffer exchange to an appropriate buffer for storage.

Figure 2:
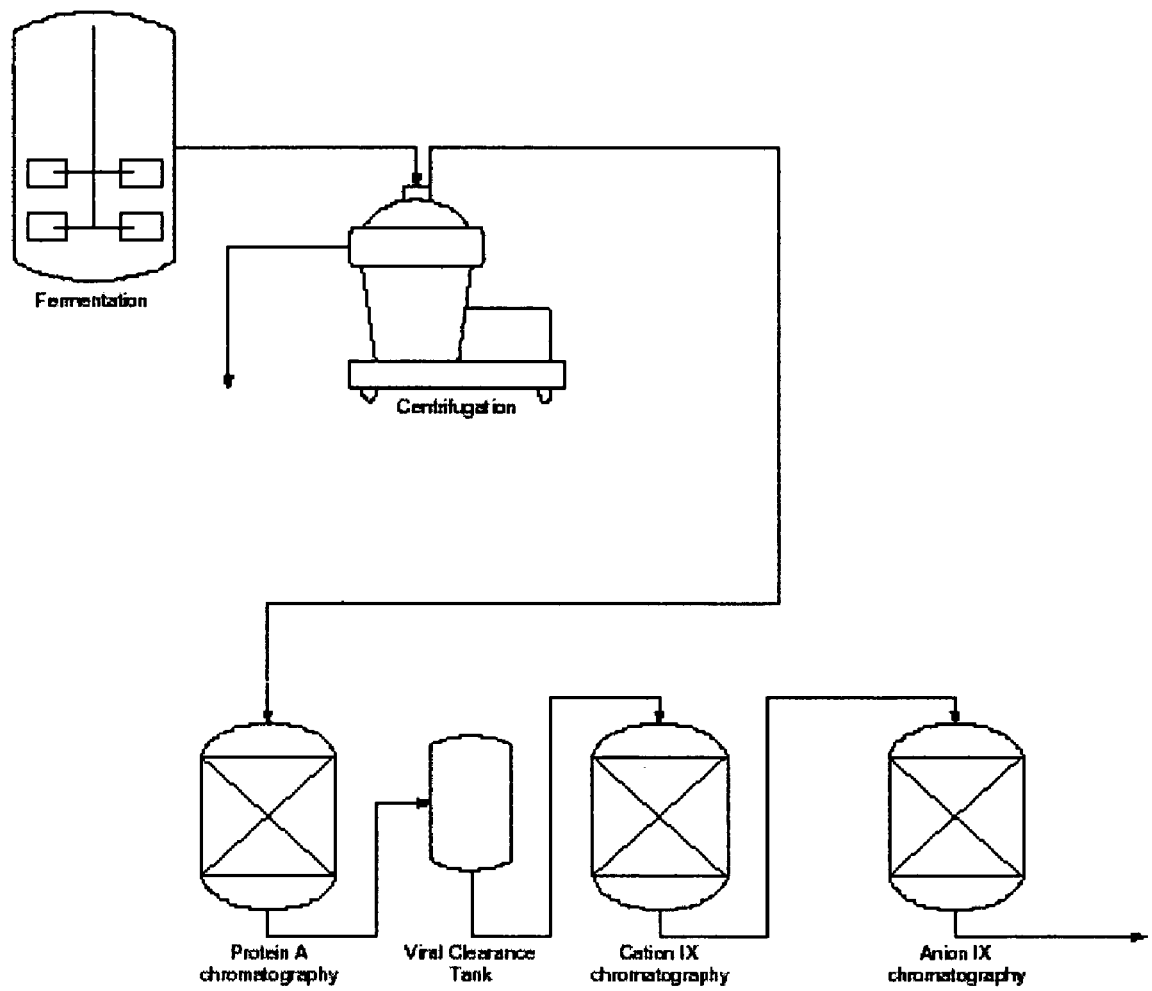
FIG. 2 depicts a flow diagram for an alternate general procedure for isolation and purification of an immunoreactive compound such as an antibody from cell culture.

An alternate process for large scale antibody production is depicted in FIG. 2. Steps in the process include: (a) Fed batch fermentation in CHO cell culture: yielding 15.000 liter of broth, containing 0.5–2 g/l of antibody; (b) centrifugation for biomass removal; (c) Protein A chromatography (main objective of this step is to remove the (majority of) host cell proteins (HCP)); (d) cation exchange chromatography (the objective of this step is to remove any Protein A ligand that has leaked from the affinity gel, since both the Protein A ligand and the antibody bind to the gel and fractionation occurs during selective elution); and (e) anion exchange chromatography (main objective is to remove (adsorb) DNA, the MAb is not adsorbed since it is fairly basic in nature).

2. Description of SMB Systems

The present invention relates to methods of using a SMB system as part of a process for the isolation and purification of immunoreactive compounds, such as antibodies or antibody fragments produced by cell culture.

In one aspect of the present invention, a SMB system may be used to separate an immunoreactive compound from host cell protein and other immaterial components employing Protein A affinity resins. In order to accommodate all steps required for reliable immunoreactive compound isolation in a Protein A affinity process, an experimental set-up which comprises zones for associating immunoreactive compound with solid phase, removing unassociated components, disassociation/elution of immunoreactive compound from solid phase and regeneration/re-equilibration of the solid phase are used.

According to this aspect of the present invention, the immunoreactive compound is associated with the Protein A module at neutral pH, unassociated components are removed in one or two wash steps, the immunoreactive compound is disassociated/eluted at low pH, and the module is regenerated and re-equilibrated by one, two or three consecutive steps. All these steps are continuously performed by a SMB system which comprises at least one module which moves through a ring which has a plurality of zones.

According to one aspect of the present invention, the ring consists of a plurality of zones, suitably from four to eight zones, depending on the number of wash and regeneration/equilibration steps used. According to the methods of the present invention, a continuous flow of purified immunoreactive compound is obtained, with the amount of solid phase and buffer used being substantially reduced in comparison with a batch mode. One aspect of the present invention is directed to using a multi-zone SMB system as described herein for antibody purification with protein A affinity adsorbents.

Protein A affinity SMB chromatography may be a powerful way to reduce the substantial cost involved in Protein A affinity chromatography. A reduction in module (or column) volume immediately translates into reduced cost of goods, additionally, smaller modules are easier to pack and usually cause fewer problems during operation. A fully automated continuous system requires much fewer operator manipulations, thus reducing the risk for failure.

According to an alternate aspect of the present invention the SMB systems described herein can also be applied to the a cation exchange chromatography step in an antibody purification process, which usually occurs after Protein A affinity chromatography step. The economic benefits of using a SMB system for this step are similar to the Protein A affinity chromatography step.

A. General Four (4) Zone SMB Systems (i) FIG. 3

Figure 3:
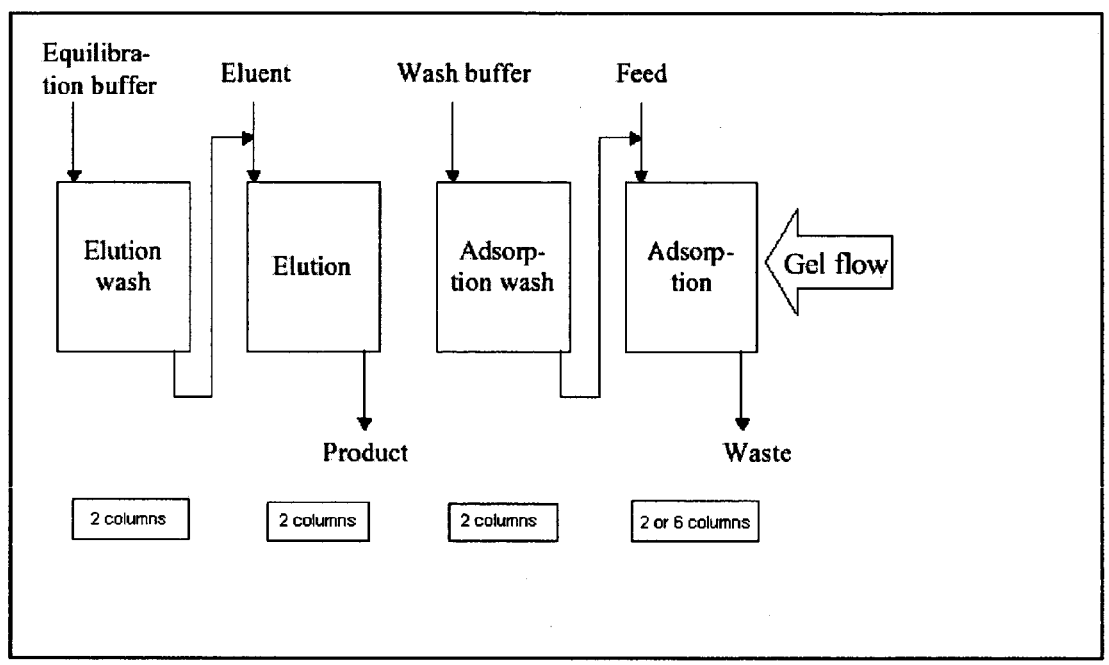
FIG. 3 depicts a diagram of a four (4) zone simulated moving bed chromatography (SMB) system of the present invention.

FIG. 3 depicts a four zone SMB system of the present invention.

According to one embodiment, the feed is applied to two (2) columns in parallel, and makes a second pass though two (2) parallel columns. Mass transfer is therefore spread over four columns. A carousel or other similar apparatus may be used to move the columns relative to stationary valves and inlet and outlet streams. The columns moving to the left from the adsorption zone enter the adsorption wash (or first wash) zone. The buffer applied here washes unbound material and removes endotoxins. The effluent of the adsorption wash (or first wash) zone is fed back into the adsorption zone to minimize product loss. The adsorption wash (or first wash) zone consists of two (2) columns in series thus reducing the amount of buffer required by about 40%. The product is eluted in an elution zone consisting of two (2) columns in series, again taking advantage of the resulting countercurrent effect. The elution zone is followed by an elution wash zone. The buffer applied in that zone may be a diluted equilibration buffer, its buffer capacity being much lower than the elution zone's buffer capacity. The elution wash buffer is recycled into the elution zone saving on water cost.

Figure 4:
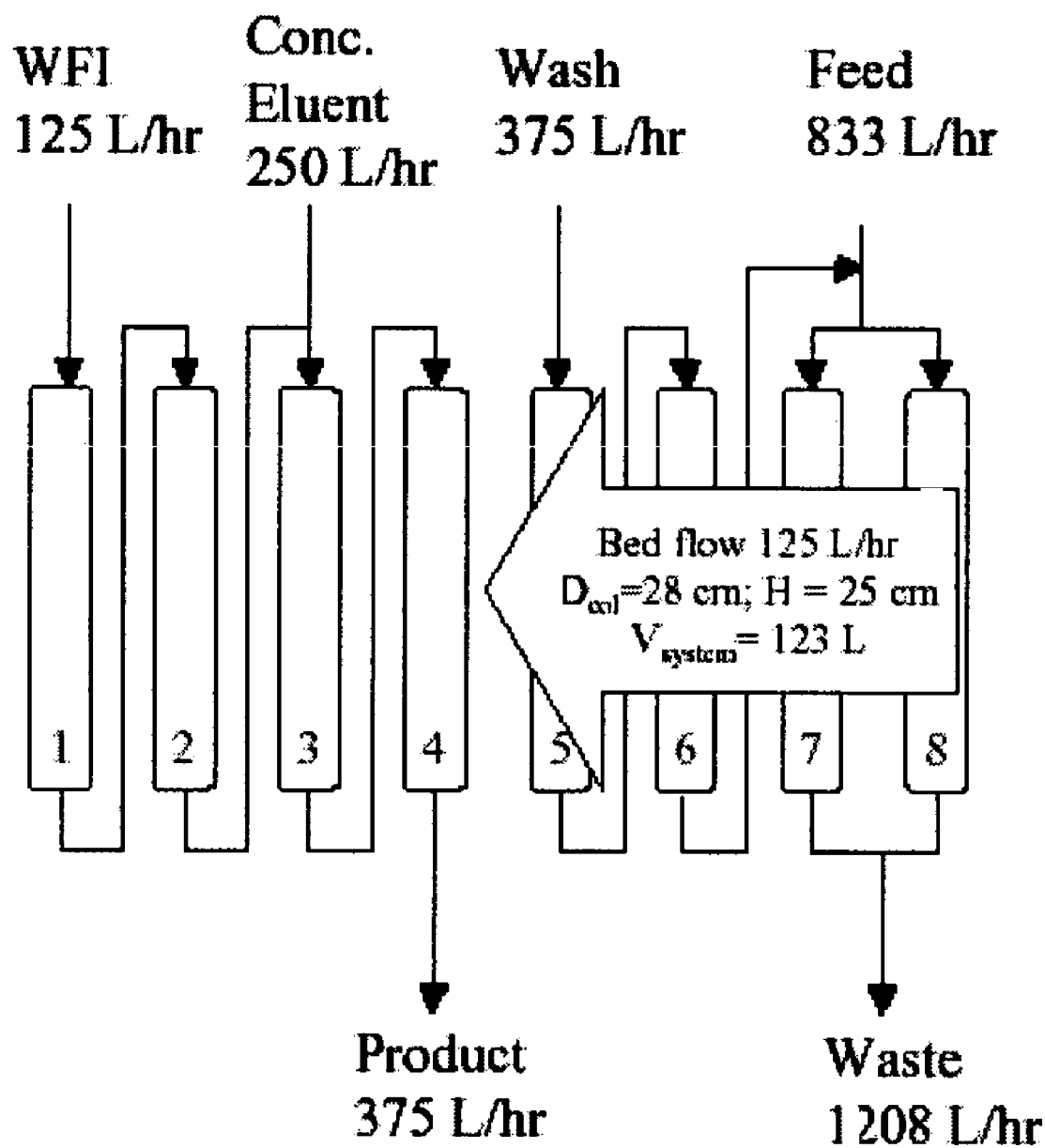
FIG. 4 depicts a diagram of an embodiment of a SMB system according to FIG. 3.

FIG. 4 depicts a process flow diagram of an alternate embodiment of the SMB system of FIG. 3, a four zone SMB system for the separation of antibody. According to this embodiment, the columns in the adsorption zone (positions 7 and 8) are connected in parallel to reduce the pressure drop. The amount of adsorbent (solid phase) in the adsorption zone is dimensioned such that mass transfer is not limiting. According to one aspect of this embodiment, the columns are arranged in a carousel. The rotation time of the carousel is set to meet the required capacity of the feed flow.

In the system depicted in FIG. 4, the wash (or first wash) zone the interstitial liquid entering from the adsorption zone is washed out and fed back into the adsorption zone. Most of the endotoxin and host cell proteins are removed here and end up in the waste stream outflow from the adsorption zone. After the wash (or first wash) zone, antibody is eluted in the elution zone; the columns at positions 3 and 4 comprise an elution zone. The columns at positions 1 and 2 comprise an elution wash zone and are used to wash out the interstitial eluent which is fed back into the elution zone thus saving eluent. In order to obtain the desired pH in the elution zone, the elution buffer applied to the elution zone in this embodiment, however, needs to be concentrated.

Figure 5:
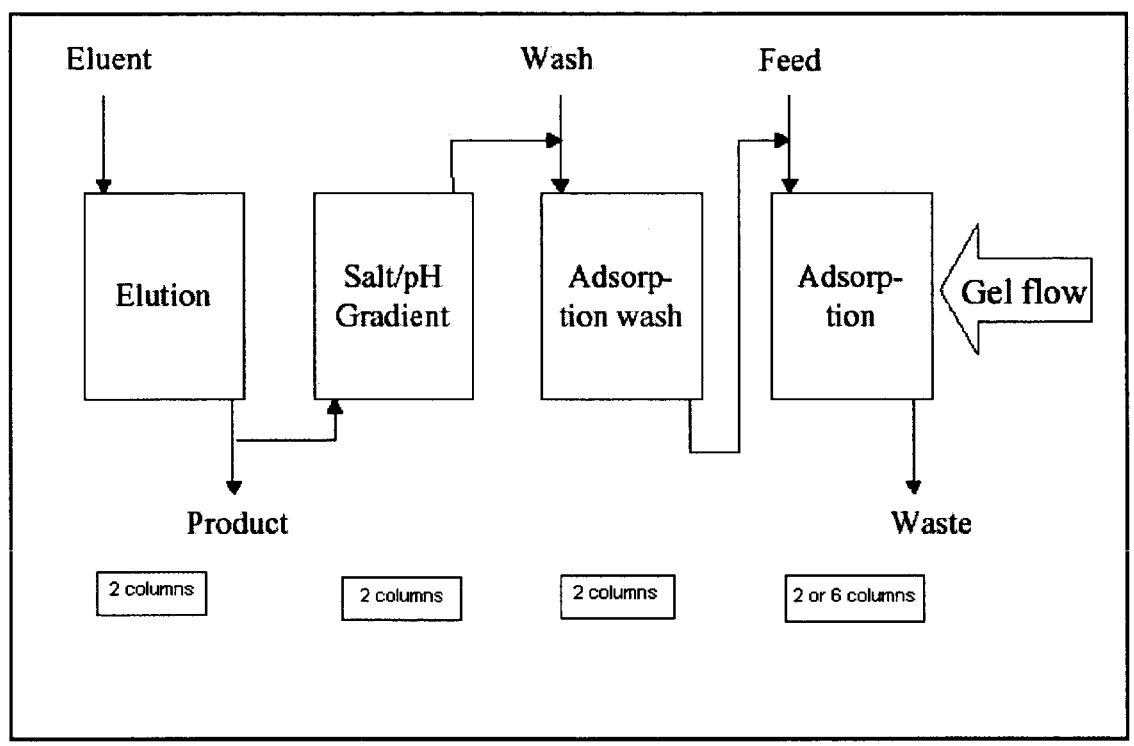
FIG. 5 depicts a diagram of an alternate four (4) zone SMB system of the present invention.

(ii) FIG. 5

FIG. 5 depicts an alternate embodiment of a four (4) zone SMB system. This system differs from the one depicted in FIG. 3.

According to one embodiment, the adsorption zone has 2 times 3 columns in parallel, thus slightly increasing the gel utilization. The adsorption zone, adsorption wash (or first wash) zone, and elution zone are basically the same as in the system of FIG. 3; however, there is no elution wash zone. This may lead to a decrease in product recovery as a small amount of eluent will enter the last column of the adsorption zone. From the product tank a small flow is pumped into a salt/pH gradient zone. This zone establishes a gradual transition in pH and salt concentration. Keeping the flow rate below the transport rate of interstitial liquid (back into the elution zone) assures that there will be minimal product loss. Presaturating the columns with eluent and product will also improve the effectivity of the elution zone.

Figure 6:
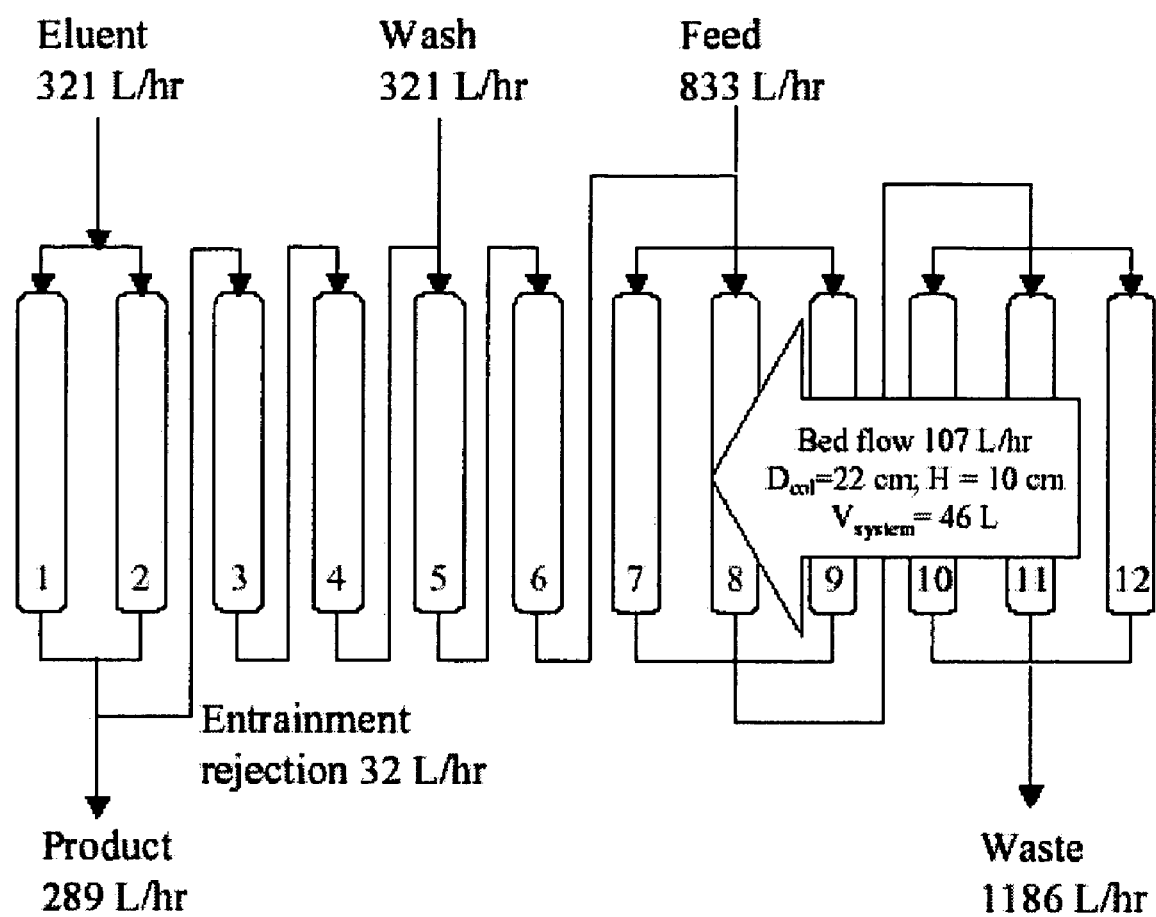
FIG. 6 depicts a diagram of an embodiment of a SMB system according to FIG. 5.

An alternate embodiment of the SMB system of FIG. 5 is depicted in FIG. 6. The principle is similar to the systems of FIGS. 3 and 4 described above, with the omission of the elution wash zone. However, one additional zone is included in this embodiment, the entrainment rejection zone. This allows for a higher effluent concentration. In addition, this zone will generate a pH profile in the system (in column positions 3 and 4). This might give a relatively smooth transition over the iso-electric point of the protein, thereby minimizing product decay.

The individual columns used for embodiment depicted in FIG. 6 may be much smaller than those used in the system of FIG. 3 or FIG. 4. The system volume and gel utilization are also significantly higher. Main reason for this is that the fraction of the gel volume which is active in the adsorption zone is higher than in the system of FIG. 3 or FIG. 4 (6 out of 12 columns instead of 2 out of 4). The absolute amount of gel in the adsorption zone is more or less the same as in the system of FIG. 3 or FIG. 4.

B. General Eight (8) Zone SMB System

Figure 7:
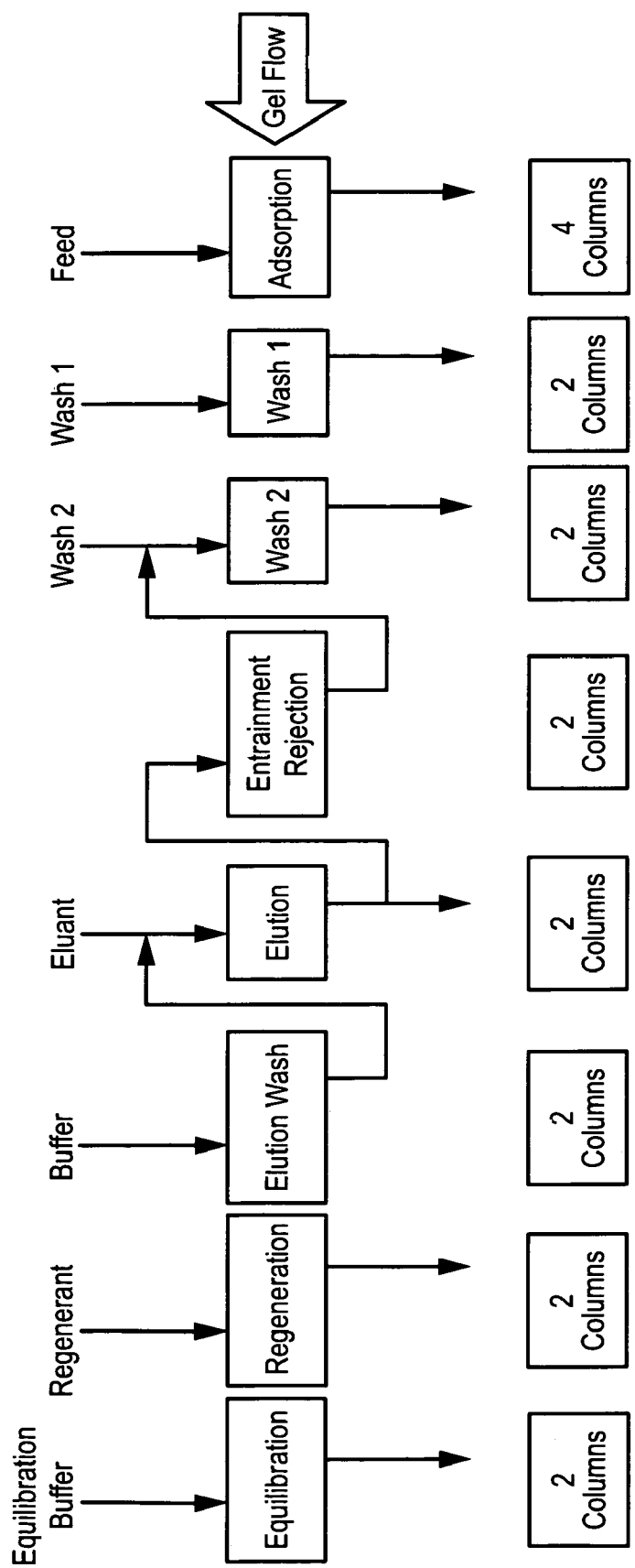
FIG. 7 depicts a diagram of an eight (8) zone SMB system of the present invention.

FIG. 7 depicts an eight (8) zone SMB system of the present invention. According to one embodiment, all process steps occur in two passes. The adsorption and elution zone have two times two parallel columns to decrease the linear flow rate. All other zones have 2 columns in series to take advantage of the countercurrent effect.

Figure 8:
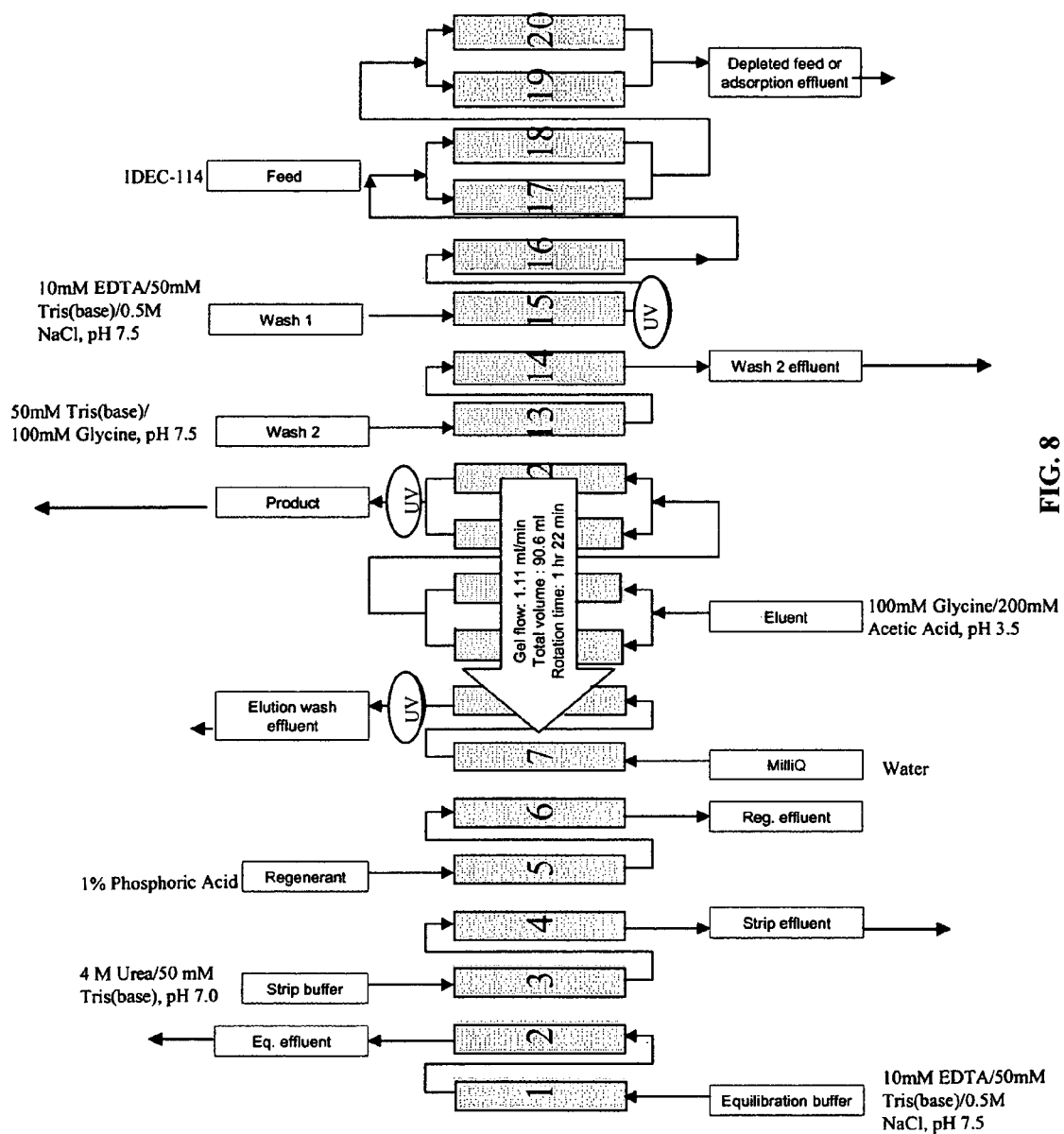
FIG. 8 depicts a diagram for an eight (8) zone simulated moving bed system of the present invention which has twenty (20) columns.
Figure 9:
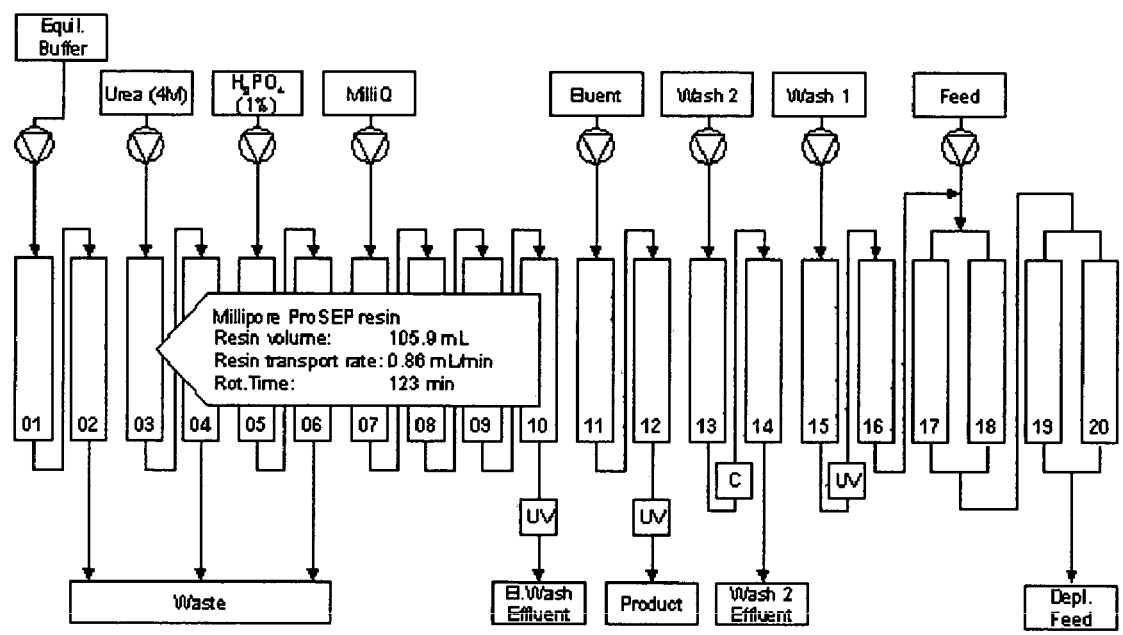
FIG. 9 depicts a diagram for an alternate embodiment of an eight (8) phase simulated moving bed system of the present invention which has twenty (20) columns.
Figure 10:
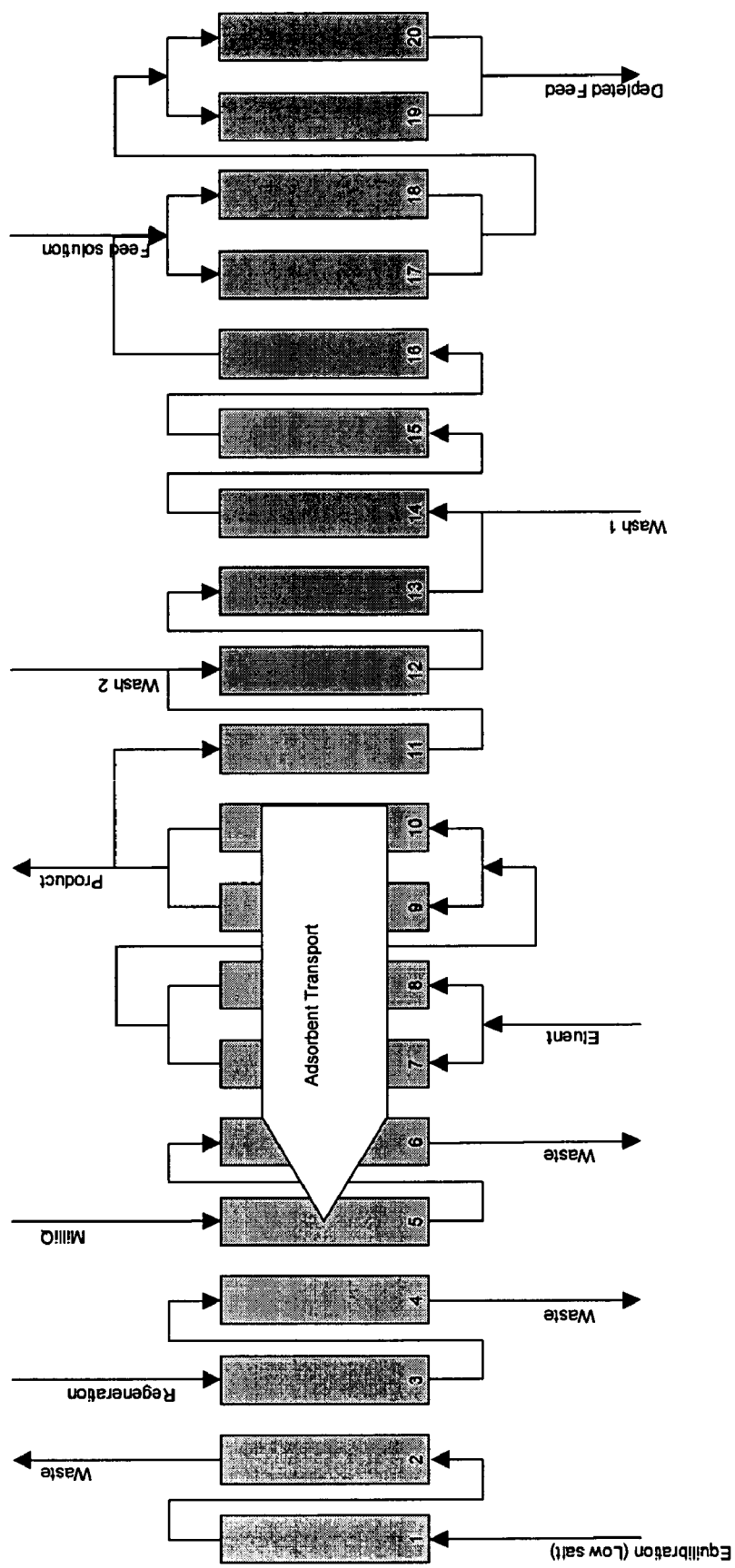
FIG. 10 depicts a diagram for an alternate embodiment of an eight (8) phase simulated invention which has twenty (20) columns.

FIGS. 8 to 10 depict alternate embodiments of eight (8) zone SMB systems of the present invention.

Example 1 describes a process run using the embodiment of FIG. 8.

Example 2 describes a process run using the embodiment of FIG. 9.

FIG. 10 depicts a diagram of an alternate embodiment of an eight (8) zone SMB system. In this embodiment, regeneration of the adsorbent has been incorporated. The system is sanitized only once per batch run, i.e. once per 15,000 liters. The adsorption zone contains four columns, which are connected as two times two parallel columns. In the first wash zone the interstitial fluid is fed back into the adsorption zone. In the first wash zone, three columns are connected in series to maximize the benefits of countercurrent contact. The first wash buffer is introduced in upflow in order to minimize the contact between high salt concentrations and concentrated MAb solutions. After a column leaves the adsorption zone, the top of the bed contains more concentrated feed solution than the bottom. In the embodiment of FIG. 10, water savings are gained from the dilution of first wash zone buffer with the effluent or buffer used for the second wash zone. The second wash zone has two columns and is designed to establish a low salt concentration at position 12 just before it moves to position 11. From the product tank a very low flow of product stream is pumped into column 11 to presaturate that column before it moves into the elution zone. The only function of position 11 is therefore product concentration, the common name for this process step is entrainment rejection. In the elution zone, elution buffer is introduced in upflow in two times two columns in parallel. The elution buffer is diluted with the elution wash buffer used to wash out the eluent from positions 5 and 6 in the elution wash zone. As a consequence, the elution buffer applied to the elution zone should be concentrated in order to compensate for the dilution effect. Columns 1 to 4 are used for equilibration and regeneration and comprises an equilibration zone and a regeneration zone. If the regeneration requires a certain concentration of sodium hydroxide, the regeneration buffer applied to the system should have a higher concentration to accommodate for the dilution. This system depicted in FIG. 10 is especially suited to a carousel type SMB system, which has the flexibility of using different flow directions in one system.

To assist in understanding, the present invention will now be further illustrated by the following examples. These Examples as they relate to the present invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Purification of a Monoclonal Antibody Using an Eight Zone Simulated Moving Bed System The simulated moving bed, SMB, technology was applied to the Protein A initial purification step of a monoclonal antibody. The system consisted of twenty columns arranged in a circle attached to a rotating carousel. Eight independent zones were established for the SMB continuous system.

A. Description of Equipment

The central valve, which consisted of three sections (top middle and bottom), delineated the eight processing zones. The top part of the valve remained stationary during the process and the inter-connections of the outlet ports defined the processing zones. The middle section of the valve was a Teflon ring that allowed the bottom section to turn freely. The bottom section of the valve was connected to the top and bottom of each column.

Each processing zone required a specific buffer and flow rate. Eight HPLC pumps were employed to deliver to the inlet sections of the top part of the valve a constant fluid flow.

The rotation of the columns was maintained by a controller that rotated the carousel at a specific interval. After a specific dwell time, the carousel rotated one spot to the next position, creating the counter current flow that reduces buffer consumption and increases resin capacity.

B. Description of Zones

In this example twenty columns were attached to the central valve. (See FIG. 8) At a snapshot in time, the columns labeled one through twenty corresponded, to the following wash zones:

(i) Equilibration Zone

Starting with column one, the Equilibration buffer (10 mM EDTA/50 mM Tris (base)/0.5M NaCl, pH 7.5) was applied to the column in upward direction. The effluent of column one was directed to the bottom of column two, the effluent of which was capture in sample vessel for future analysis.

(ii) Regeneration Zone

Regeneration buffer (4M Urea/50 mM Tris(Base) pH 7.0) was being applied to column three in the downward direction. The effluent of column three was directed to the top of column four, the effluent of which was captured in a sample vessel for future analysis.

(iii) CIP Zone

Clean in place, CIP zone buffer (1% Phosphoric acid) was applied in the downward direction to the top of column five. The effluent of column five column was directed to the top of column six, the effluent of which was captured in a sample vessel for future analysis.

(iv) Elution Wash Zone

Purified water (MilliQ) was applied in the upward direction to column seven, the effluent of which was applied to column eight in the upward direction. The effluent of column eight was monitored by a UV meter and collected in a sample vessel for future analysis.

(v) Elution Zone

Elution zone buffer (100 mM Glycine/200 mM Acetic Acid pH 3.5) was applied in an upward direction to both column nine and column ten in a parallel manner. The effluent of column nine and ten were combined into a single stream that was then split to wash column eleven and twelve in an upward manner. The effluent of column eleven and column twelve were combined to form the product stream, which was monitored by a UV meter and collected in a sample vessel for future analysis.

(vi) Second Wash Zone

Second wash zone buffer (50 mM Tris(base)/100 mM Glycine pH 7.5) was applied in a downward direction to column thirteen. The effluent of column thirteen was applied in a downward flow to column fourteen, the effluent of which was captured in a sample vessel for future analysis.

(vii) First Wash Zone

First wash zone buffer (10 mM EDTA/50 mM Tris(base)/0.5M NaCl) was applied in a downward direction to column fifteen. The effluent of column fifteen was monitored by a UV meter and then applied to column sixteen in a downward direction. The effluent of column sixteen was combined with the Feed stream.

(viii) Adsorption Zone

The feed stream, which contained a mixture of host cell protein and monoclonal antibody and other components, was mixed online with the effluent of column sixteen. The new stream was then split and applied in parallel to both column seventeen and column eighteen in a downward direction. The effluent of column seventeen and column eighteen were mixed and then split and applied in parallel to column nineteen and column twenty in a downward direction. The effluent of column nineteen and column twenty were combined and collected in sample vessel for future analysis.

C. Description of Processing

The Description of Zones by a column number set forth hereinabove represents a snapshot in time. After the specified dwell time had elapsed, the carousel rotated one step in a clockwise direction. As an example, this means that column one, which previously was exposed to equilibration buffer in a downward direction was now in the position that column twenty was previously occupying. Consequently, column twenty was now located where column nineteen use to be, and so on for the entire column set. From a processing stand point this means that the effluent of column nineteen and column eighteen were combined then split and applied in the downward direction to column twenty and column one. The column rotation continued until there is no more feed left to process.

Each zone described in the Description of Zones had a specific purpose in the processing of the feed. Starting from the CIP zone, the regeneration step was implemented as a process-cleaning step. The Regeneration Zone follows to ensure that any non-specifically bound compounds were dissociated from the resin. The Equilibration Zone was implemented to displace the Regeneration Zone buffer and to create an environment in the column that would permit antibody binding during the initial loading period. In the Adsorption Zone, the feed stream introduced the desired product to the column. The First Wash Zone displaced the loading feed and washed out non-specific proteins and other impurities. The Second Wash Zone was implemented to bring the conductivity to an acceptable base line. The Elution Zone was created to dissociate the antibody from the Protein-A ligand and collect the antibody. The Elution Wash Zone was a test section to check whether all the antibody was effectively washed out during the Elution Zone.

Since process economics are dependent on the volume of buffer consumed during processing, experimentation was performed to determine the minimal amount of buffer needed to perform the above-mentioned task assigned to each zone. Table I describes the range of column volumes tested for each section.

TABLE I

| Stream | Column volumes |
| --- | --- |
| Regenerant | 2.9 |
| Strip | 2.5 |
| Equliibration | 1.9–3.0 |
| Feed | 16.7–20.4 |
| Wash 1 | 3.5 |
| Wash 2 | 1.9–2.5 |
| Elution | 0.9–3.9 |
| Elution wash | 0.95–1.9 |

B. Results

A summary of the relative amounts of product, Host cell protein (HCP), and Gentamicin found in the process streams is shown in Table II below.

TABLE II

| Stream | Product (%) | Host cell protein (%) | Gentamicin (%) |
| --- | --- | --- | --- |
| Depleted feed | 4.5 | 78.3 | 43.6 |
| Wash 1 effluent | NA | NA | NA |
| Wash 2 effluent | 0.4 | 0.1 | 0.01 |
| Eluent/Product | 83.8 | ~0.1% | 0.03 |
| Eluent wash effluent | 0.2 | ~0 | ~0 |
| Regenerant effluent | NA | NA | NA |
| Strip effluent | ~0 | ~0.1 | ~0 |
| Equliibration effluent | NA | ~0.1 | NA |
| Total | 88.9 | 78.7 | 43.6 |

NA—Not Available. For the case of Wash 1, this stream is combined with the feed stream, and as such, is not measured separately.

A protein recovery of 83.8% was achieved using the SMB process described in this Example. The unaccounted amounts of product are likely to be found in the regenerant fractions. The antibody concentration in product pool was ~8.6 times higher than in the feed stream. The quality of the product in terms of monomer content and antibody integrity was investigated by SEC and CE-SDS and shown to have values comparable to batch Protein-A chromatography There was a 3.05 log reduction in HCP (>99.9% removal) and a 3.46 log reduction of gentamicin (>99.96% removal) in the elution pool. The HCP concentration was very similar to results from a conventional protein-A chromatography scale-up run. The gentamicin levels were four times lower.

Example 2

Purification of a Monoclonal Antibody Using an Alternate Eight Zone Simulated Moving Bed System A Simulated Moving Bed System which was similar to the SMB system described in Example 1 was used to purify an antibody. This system also consisted of twenty (20) columns arranged in a circle attached to a rotating carousel. Eight independent zones were established for the SMB continuous system. A diagram of this system is depicted in FIG. 9.

The configuration of this system differed from that described in FIG. 8 in (a) that all columns operated in downflow and (b) that the elution wash zone used four (4) columns in series and the elution zone used two (2) columns in series.

Example 3

Demonstration of Reproducibility of Antibody Purification

Figure 11:
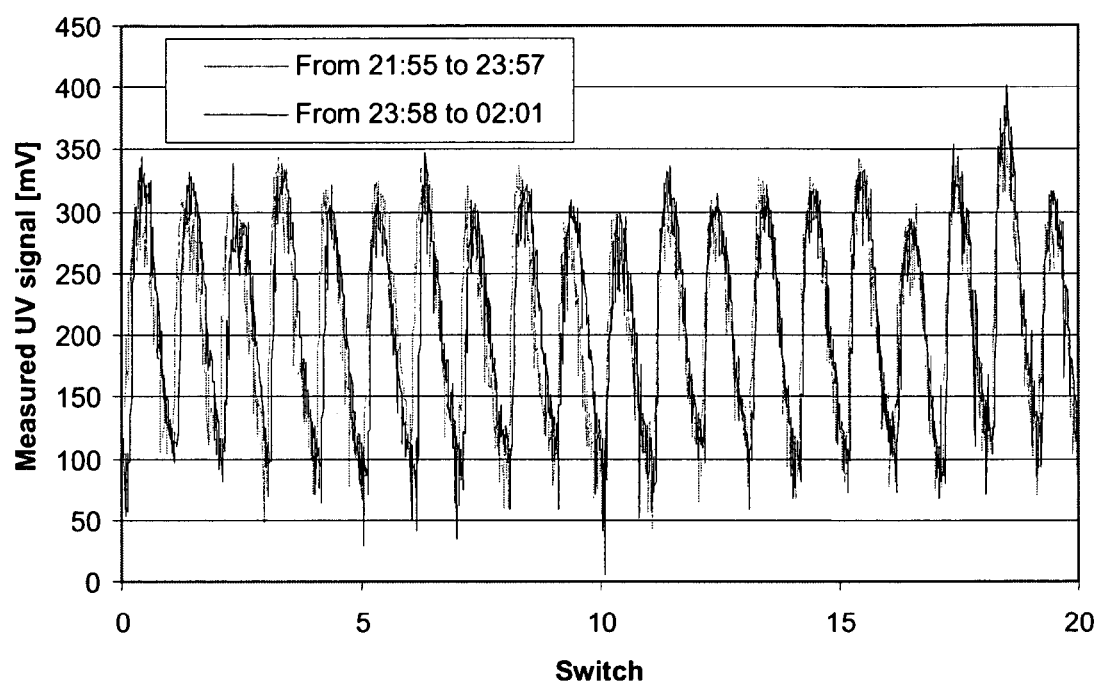
FIG. 11 depicts a UV trace from Wash 1 for a series of twenty (20) column switches within one rotation of the SMB apparatus depicted in FIG. 9 as described in Example 3.

The Simulated Moving Bed System described in Example 2 (and depicted in FIG. 9) was used to examine the reproducibility of the present antibody purification process. In a SMB system reproducibility is required both in between the individual columns (in this case 20 columns), and in between SMB cycles (rotations). Reproducibility in between columns is shown in FIG. 11 by comparing the UV traces from Wash 1. The detector is depicted in FIG. 9 as UV between columns 15 and 16. The signal from this detector is shown for 20 column switches, representing Wash 1 from 20 individual columns in this particular position for two independent rotations of the SMB cycle. As can be seen from FIG. 11, the signals recorded are consistent from all 20 switches and even overlap for two independent rotations, thus demonstrating column to column reproducibility of the purification.

Figure 12:
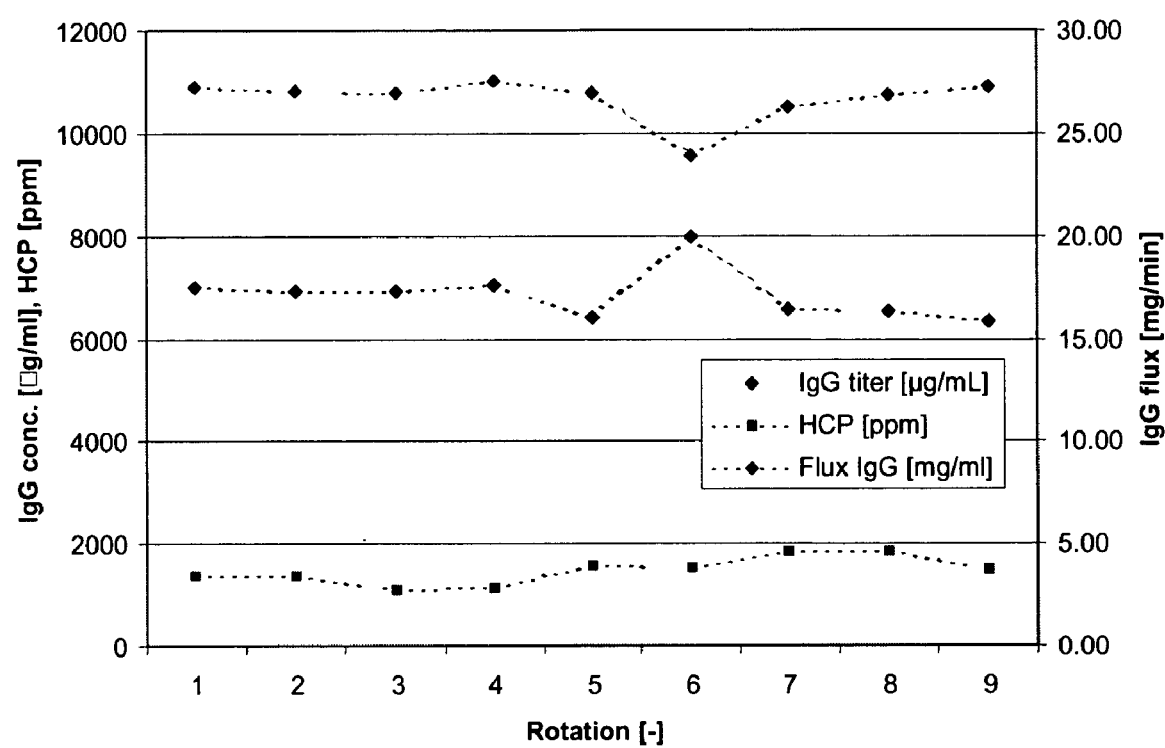
FIG. 12 depicts a plot of antibody concentration (IgG titer), IgG flux and concentration of host cell proteins (HCP) for nine (9) full rotations of the SMB system depicted in FIG. 9. In this figure the top plot of diamonds (♦) depicts IgG flux; the lower plot of diamonds (♦) depicts IgG titer; and the plot of the squares (■) depict HCP

The reproducibility between rotations (of the 20 column system) is shown in FIG. 12. FIG. 12 depicts a plot of antibody concentration (IgG titer), IgG flux, and concentration of host cell proteins (HCP is shown for 9 full rotations of the SMB system. IgG flux (mg/ml) was depicted by the top plot of diamonds (♦). IgG titer (mg/ml) was depicted by the lower plot of diamonds (♦). HCP (ppm) was depicted by the plot of squares (■).

We claim:

1. A method of separating an antibody or antibody fragment from at least one immaterial component in a fluid mixture, comprising:
    (a) providing a simulated moving bed (SMB) chromatography apparatus that comprises a plurality of modules in fluid conducting communication with said apparatus, wherein said modules comprise at least one solid phase comprising a ligand for which the antibody or antibody fragment has selective affinity, and wherein said apparatus comprises a plurality of zones through which the modules pass;
    (b) introducing the fluid mixture into a module in an association zone wherein the fluid mixture contacts the solid phase in a countercurrent mode and the antibody or antibody fragment associates with the solid phase;
    (c) introducing a wash buffer into the module comprising the associated antibody or antibody fragment in at least one wash zone, wherein the wash buffer contacts the solid phase and substantially removes at least one immaterial component from said module;
    (d) introducing an eluent into the module comprising the associated antibody or antibody fragment from step (c) in an elution zone, wherein the eluent contacts the solid phase and promotes disassociation of the antibody or antibody fragment from the solid phase;
    (e) removing the antibody or antibody fragment that is substantially separated from at least one immaterial component in said fluid mixture;
    (f) introducing an elution wash buffer into the module from step (e) in an elution wash zone;
    (g) introducing a solution comprising a regenerant into the module from step (f) in a regeneration zone; and
    (h) introducing an equilibration buffer into the module in an equilibration zone, wherein the equilibration buffer creates an environment in the module that permits binding of the antibody or antibody fragment to the solid phase comprising the ligand.

2. A method according to claim 1, wherein step (g) comprises introducing a regeneration buffer comprising urea into the module.

3. A method according to claim 1, wherein step (g) comprises introducing a clean in place (CIP) solution into the module.

4. A method according to claim 3, wherein the CIP solution comprises phosphoric acid.

5. A method according to claim 1, wherein the antibody or antibody fragment comprises a constant region of an immunoglobulin and the solid phase comprises Protein A or Protein G.

6. A method according to claim 5, wherein the eluent comprises an acidic buffer.

7. A method according to claim 1, wherein effluent of a module in at least one wash zone is fed back into a module in the association zone.

8. A method according to claim 1, wherein step (c) of said method comprises introducing a high salt wash buffer into a module comprising the associated antibody or antibody fragment in a first wash zone.

9. A method according to claim 8, wherein step (c) of said method further comprises introducing a low salt wash buffer into a module comprising the associated antibody or antibody fragment in a second wash zone.

10. A method according to claim 1, further comprising a step following wash step (c) that comprises introducing solution containing purified antibody or antibody fragment into a module in an entrainment rejection zone prior to elution of antibody or antibody fragment from said module.

11. A method according to claim 1, wherein the concentration of antibody or antibody fragment obtained in step (e) is greater than the concentration of antibody or antibody fragment in the fluid mixture that is introduced in step (a).

* * * * *